United States Patent [19]

Oshiyama et al.

[11] Patent Number: 5,117,903
[45] Date of Patent: Jun. 2, 1992

[54] MULTITUBE HEAT EXCHANGER WITH UNIFORM-FLOW BAFFLES IN HEAD CHAMBER

[75] Inventors: Hiroaki Oshiyama; Atsuhiko Nogawa, both of Fuji; Satoru Sakai, Fujinomiya, all of Japan

[73] Assignee: Terumo Kabushiki Kaisha, Tokyo, Japan

[21] Appl. No.: 457,784

[22] PCT Filed: Jul. 12, 1988

[86] PCT No.: PCT/JP88/00692

§ 371 Date: Mar. 12, 1990

§ 102(e) Date: Mar. 12, 1990

[87] PCT Pub. No.: WO89/00669

PCT Pub. Date: Jan. 26, 1989

[30] Foreign Application Priority Data

Jul. 13, 1987 [JP] Japan .................. 62-173003

[51] Int. Cl.⁵ .................. F28F 13/12; F28F 9/24
[52] U.S. Cl. .................. 165/158; 165/174; 422/46
[58] Field of Search .................. 165/174, 158, 47; 422/44, 46, 48

[56] References Cited

U.S. PATENT DOCUMENTS

| | | | |
|---|---|---|---|
| 1,557,838 | 10/1925 | Hiller | 165/174 |
| 2,044,455 | 6/1936 | Witzel | 165/174 |
| 2,655,346 | 10/1953 | Corbitt et al. | |
| 2,715,516 | 8/1955 | Reinold et al. | 165/158 |
| 3,315,738 | 4/1967 | Jones et al. | 165/174 |
| 3,407,875 | 10/1968 | Campbell | 165/174 |
| 3,802,496 | 4/1974 | Ris et al. | 165/174 |
| 4,047,563 | 9/1977 | Kurata | 165/158 |
| 4,458,750 | 7/1984 | Huber | 165/174 |
| 4,857,144 | 8/1989 | Casparian | 165/174 |

FOREIGN PATENT DOCUMENTS

| | | | |
|---|---|---|---|
| 0897711 | 7/1949 | Fed. Rep. of Germany | 165/174 |
| 1501484 | 4/1966 | Fed. Rep. of Germany | |
| 2303788 | 1/1973 | Fed. Rep. of Germany | |
| 1583744 | 12/1967 | France | |
| 0215155 | 10/1984 | German Democratic Rep. | 165/174 |
| 0425461 | 10/1947 | Italy | 165/174 |
| 52-111956 | 8/1977 | Japan | |
| 54-99159 | 7/1979 | Japan | |
| 57-90146 | 6/1982 | Japan | |
| 58-14803 | 3/1983 | Japan | |
| 59-97388 | 7/1984 | Japan | |
| 61-20559 | 1/1986 | Japan | |
| 61-9642 | 3/1986 | Japan | |
| 0295957 | 2/1971 | U.S.S.R. | 168/174 |
| 0934766 | 10/1982 | U.S.S.R. | 165/158 |
| 1288484 | 2/1987 | U.S.S.R. | 165/158 |

*Primary Examiner*—John K. Ford
*Attorney, Agent, or Firm*—Frishauf, Holtz, Goodman & Woodward

[57] ABSTRACT

A multitube heat exchanger is used as a heat exchanger for blood in an artificial lung, for example. The multitube heat exchanger has a number of pipes disposed in a tubular housing and heads mounted on the opposite ends of the housing and having fluid inlet and outlet ports, respectively. A fluid flows through the pipes. The housing has fluid inlet and outlet holes for passing another fluid around the pipes. One of the heads which has the fluid inlet port accommodates baffle plates for checking the fluid flow to produce a turbulent fluid flow. With this arrangement, no air bubbles remain trapped in the head with the fluid inlet port, and the fluid can uniformly distributed into the pipes to keep a uniform temperature within the heat exchanger.

3 Claims, 5 Drawing Sheets

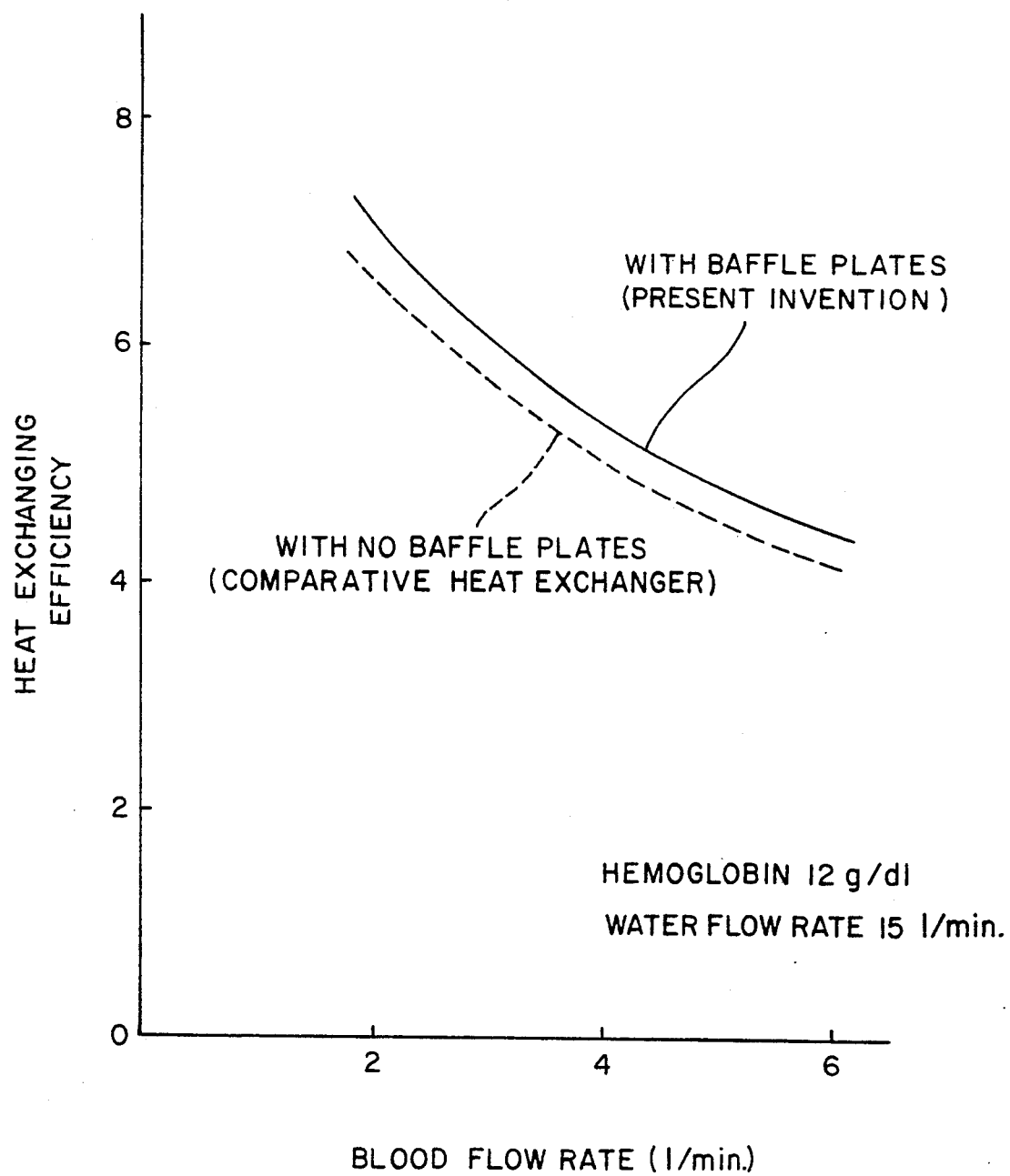

MULTITUBE HEAT EXCHANGER WITH UNIFORM-FLOW BAFFLES IN HEAD CHAMBER

TECHNICAL FIELD

The present invention relates to a multitube heat exchanger having a number of pipes juxtaposed in a tubular housing, and more particularly to a small-size multitube heat exchanger having a small effective heat-exchanging area, the heat exchanger being capable of uniformly distributing and supplying a fluid into the pipes of the heat exchanger.

BACKGROUND ART

There have widely been used multitube heat exchangers having a tubular housing including heads defined by partitions in the opposite sides of the tubular housing. One of the heads has a fluid inlet port and the other head has a fluid outlet port. The housing accommodates a number of pipes juxtaposed between the heads for passing a fluid therethrough. The housing has fluid inlet and outlet holes for passing another fluid around the tubes, so that heat can be exchanged between the fluids through the walls of the tubes. If a multitube heat exchanger of this type is reduced in size for use as a heat exchanger for an artificial lung or the like, for example, the volumes of the heads are relatively large as compared with the effective heat-exchanging area of the heat exchanger. As a result, the speed of flow of the fluid in the pipes is greatly affected by the position of the pipes because of the directivity of the fluid flowing into one of the heads. Particularly, if the inlet port of the head is oriented tangentially to the tubular housing, the fluid produces a swirling motion in the head due to its directivity, thus developing a pressure difference between the central and outer circumferential regions in the head. Therefore, the speed of flow of the fluid flowing in those pipes which are located in the central region largely differs from the speed of flow of the fluid flowing in those pipes which are located in the outer circumferential region, with the result that the temperature in the heat exchanger becomes ununiform. The fluid in the central pipes does not flow, and hence a heat exchange between the fluid in the central pipes and the other fluid flowing around the central pipes is ineffective, and hence the efficiency of the entire heat exchanger is low. It is thus difficult to control the temperature of the other fluid in its entirety. Air bubbles introduced into the inlet port of the head tend to be attracted to the central lowerpressure region in the head. Consequently, these air bubbles are liable not to be discharged out through the pipes, making the temperature in the heat exchanger more uneven.

DISCLOSURE OF THE INVENTION

In view of the aforesaid drawbacks of the conventional multitube heat exchangers, it is an object of the present invention to provide a multitube heat exchanger which can remove air bubbles trapped in the central region in a head with a fluid inlet port and which prevents the speed of flow of a fluid in the pipes from flowing at different speeds depending on the position of the pipes, so that the fluid can uniformly distributed into the pipes to uniformize the temperature in the heat exchanger.

To achieve the above object, there s provided a multitube heat exchanger including a tubular housing having partitions on opposite ends thereof which form heads, respectively, one of the heads having a fluid inlet port and the other head having a fluid outlet port, and a plurality of juxtaposed pipes extending between the heads for passing a fluid therebetween, the housing having fluid inlet and outlet holes for passing another fluid around the pipes, for effecting a heat exchange between the fluids through walls of the pipes, characterized in that the head which has the fluid inlet port accommodates projections for reducing the directivity of the fluid introduced from the fluid inlet port to substantially uniformize the rate of flow of the fluid introduced into the pipes.

The fluid inlet port is open tangentially to the housing.

The projections comprise baffle plates.

The projections comprise a plurality of baffle plates for generating a turbulent flow in the fluid introduced from the fluid inlet port, the baffle plates being disposed in the head which has the fluid inlet port and angularly spaced from each other.

Each of baffle plates projects in the axial direction of the head.

BRIEF DESCRIPTION OF THE DRAWINGS

FIG. 6 is a graph showing the relationship between the rate of a blood flow and the heat-exchanging efficiency, by way of example, of a heat exchanger according still another embodiment of the invention and a conventional multitube heat exchanger.

BEST MODE FOR CARRYING OUT THE INVENTION

Preferred embodiments of a multitube heat exchanger according to the present invention will be described in detail with reference to the accompanying drawings.

Figure 1:
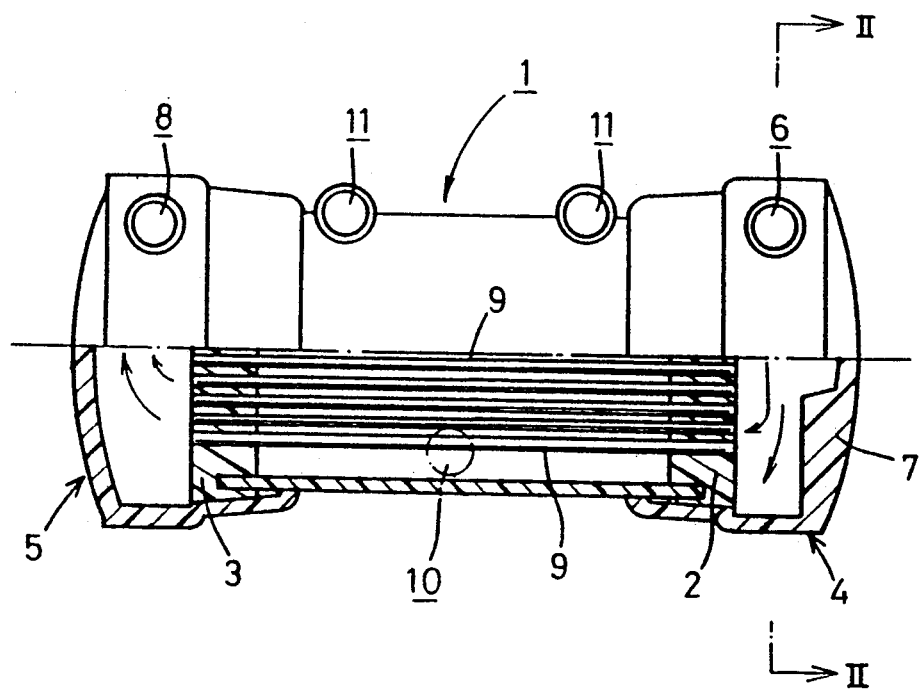
FIG. 1 is a side elevational view, partly in cross section, of a heat exchanger according to the present invention.
Figure 2:
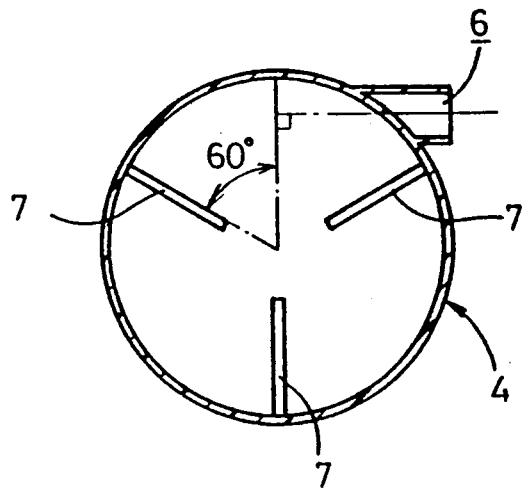
FIG. 2 is a cross-sectional view taken along line II—II of FIG. 1.

As shown in FIG. 1, a multitube heat exchanger according to the present invention includes a tubular housing 1 with partitions 2, 3 attached to its opposite open ends and heads 4, 5 mounted on the opposite ends of the housing 1. The head 4 has a fluid inlet port 6 and a plurality of projections, e.g., baffle plates 7. As shown in FIG. 2, the baffle plates 7 are spaced a certain distance from the center of the inner side surface of the head 4 and extend in the axial direction of the head 4. The baffle plates 7 also extend radially outwardly and terminate at the inner circumferential surface of the head 4. The baffle plates 7 are angularly spaced from each other by 120°. In order for the baffle plates 7 to check the flow of a fluid introduced from the inlet port 6, one of the baffle plates 7 is inclined at 60°, for example, to a radial direction normal to the direction (tangential direction) in which the inlet port 6 is oriented.

The other head 5 has a fluid outlet port 8. The housing 1 accommodates therein a plurality of pipes 9 juxtaposed between the heads 4, 5 and extending through the partitions 2, 3. The fluid is introduced from the inlet port 6 of the head 4 into the heat exchanger, flows through the pipes 9, and is discharged from the outlet port 8 of the head 5. The housing 1 has inlet and outlet holes 10, 11 defined in its outer circumference for passing another fluid around the pipes 9.

Figure 3A:
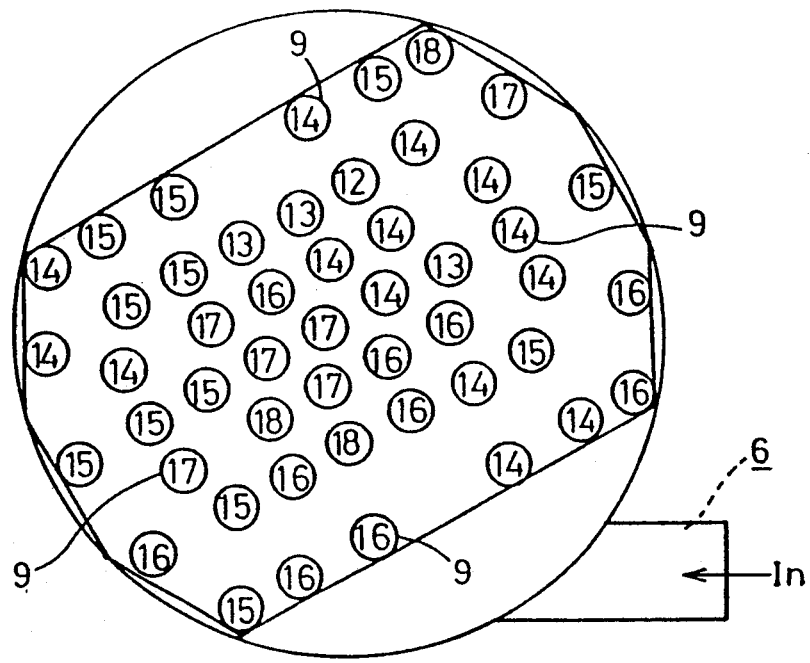
FIG. 3(a) is a diagram illustrative of discharge pressures in the pipes of the heat exchanger.
Figure 3B:
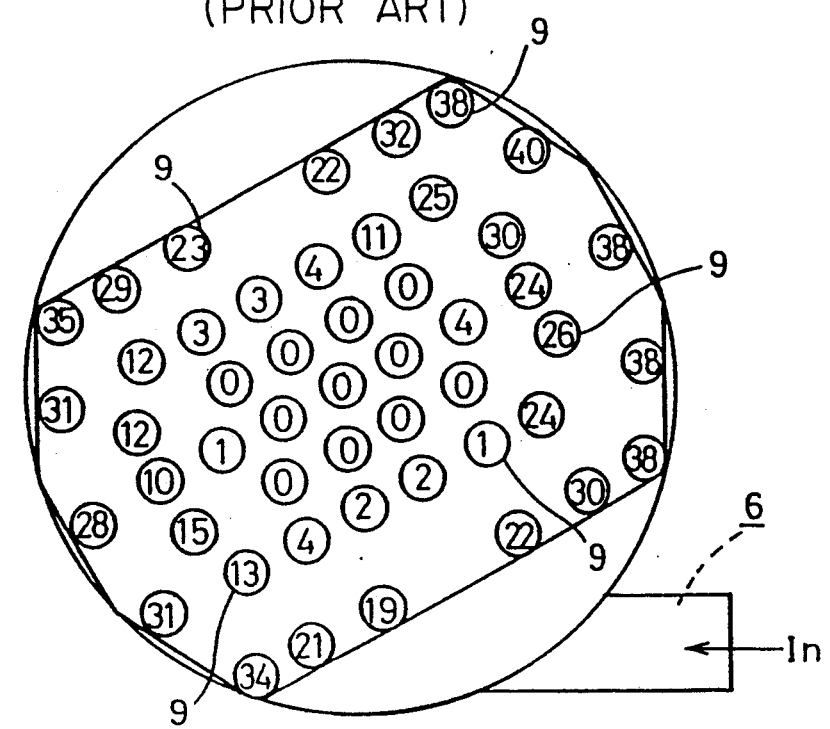
FIG. 3(b) is a diagram illustrative of discharge pressures in the pipes of a heat exchanger with no baffle plates employed according to a comparative example.

The inventor conducted an experiment in which a heat-exchanging medium was introduced from the inlet port 6 into the head 4 at a rate of 22 l/min. In the experiment, the removal of air bubbles was observed and the discharge pressures (mmHg) at the outlet ends of the pipes were measured. The same observation and measurement were also carried out on a heat exchanger having no baffle plates 7 according to a comparative example. The results of the experiment are shown in FIGS. 3(a) and 3(b) and Table 1 below. FIG. 3(a) shows the results of the measurement of the heat exchanger of the present invention, and FIG. 3(b) shows the results of the measurement of the comparative heat exchanger. The numerical values in the pipes 9 represent discharge pressures:

TABLE 1

|  | Comparative heat exchanger | Inventive heat exchanger |
| --- | --- | --- |
| Air bubble removal | Introduced air bubbles remained trapped in the center of the head | Introduced air bubbles flew out quickly |
| Discharge pressure | Varied in the range from 0 to 30 mmHG | Held within 6 mmHG |
| Total flow rate (l/min) | 17 | 19.3 |
| Heat-exchanging efficiency (Pf) | About 0.50 | About 0.55 |

The Pf (Performance factor) was calculated according to the following equation:

$$Pf = (Tbo - Tbi)/(Twi - Tbi)$$

where

Tbo: the temperature of the fluid having been subjected to a heat exchange and discharged from the heat exchanger (°C.);

Tbi: the temperature of the fluid entering the heat exchanger and to be subjected to a heat exchange (°C.);

Twi: the temperature of a heat medium (e.g., water) entering the heat exchanger (°C.).

The Pf indicates how the temperature varies while the fluid to be subjected to a heat exchange is passing through the heat exchanger. As can easily be understood from Table 1, the heat exchanger of the invention has a higher heat-exchanging efficiency than that of the comparative heat exchanger, and hence has a better heat-exchanging capability.

According to this embodiment, the flow of the fluid introduced from the inlet port 6 is checked and converted to a turbulent flow by the baffle plates 7, thus impairing the directivity of the fluid. The fluid is therefore introduced uniformly into the pipes 9, and air bubbles are prevented from remaining in the central region in the head 4.

Figure 4:
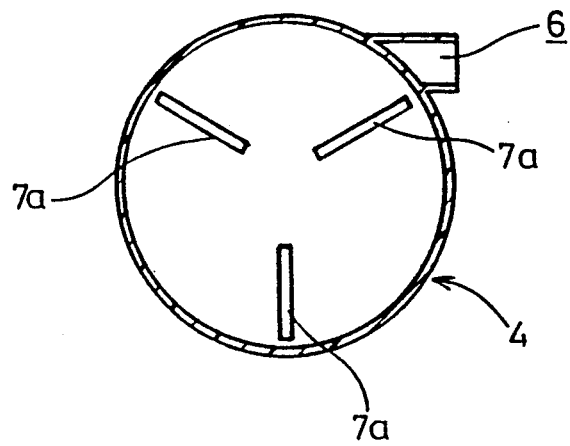
FIG. 4 is a transverse cross-sectional view showing baffle plates according to another embodiment of the present invention.

A heat exchanger according to another embodiment of the present invention will be described below. In this second embodiment, baffle plates 7a (see FIG. 4) are disposed in the head 4 of the heat exchanger shown in FIG. 1. The baffle pates 7a are of substantially the same construction as that of the baffle plates 7 described above, except that the baffle plates 7 have ends terminate short of the inner circumferential surface of the head 4.

Figure 5A:
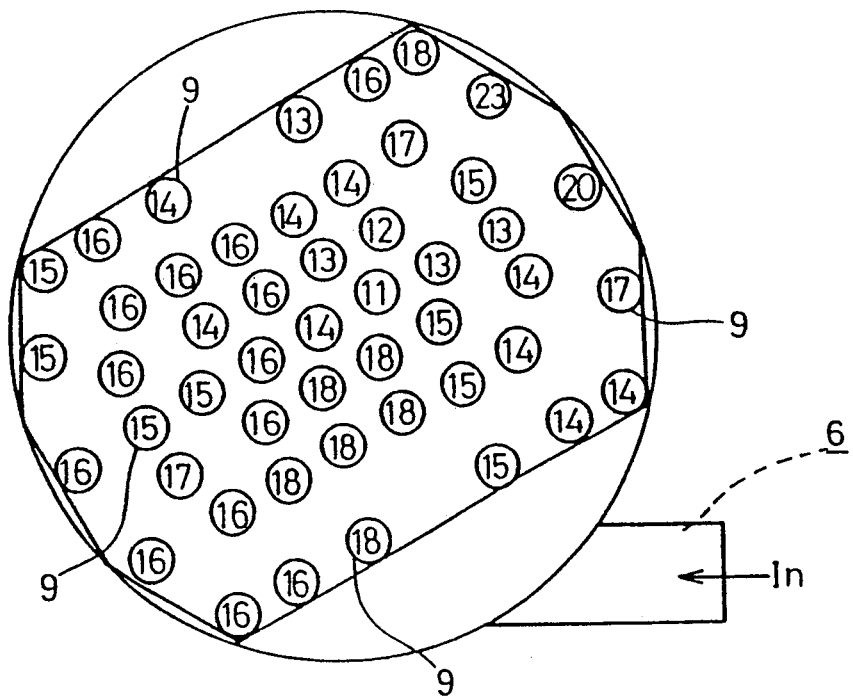
FIG. 5(a) is a diagram illustrative of discharge pressures in the pipes with the baffle plates shown in FIG. 4 being employed.
Figure 5B:
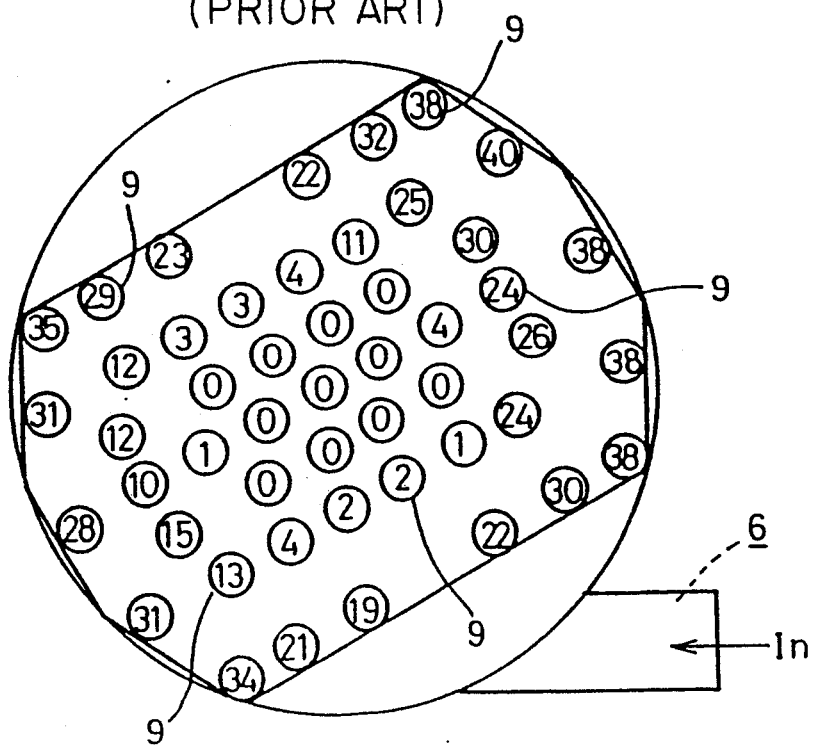
FIG. 5(b) is a diagram illustrative of discharge pressures in the pipes of a heat exchanger with no baffle plates employed.

As with the first embodiment, a fluid was introduced from the inlet port 6 of the head 4, and discharge pressures (mmHg) at the outlet ends of the pipes 9 were measured. The same measurement was also effected on a heat exchanger having no baffle plates 7a according to a comparative example. The results of the experiment are shown in FIGS. 5(a) and 5(b). FIG. 5(a) shows the results of the measurement of the heat exchanger of the present invention, and FIG. 5(b) shows the results of the measurement of the comparative heat exchanger. The numerical values in the pipes 9 represent discharge pressures (mmHg).

As with the second embodiment, the fluid flows substantially uniformly through the pipes 9 of the heat exchanger according to the second embodiment. However, no fluid at all flowed through the pipes 9 in the central region in the comparative heat exchanger. The baffle plates 7a are effective in reducing the pressure loss, making it possible to reduce the resistance and assuring a smooth fluid flow. The total rate of flow and the pressure loss of the comparative and inventive heat exchangers when the heat-exchanging medium is introduced using pumps of the same capacity are given in following Table 2:

TABLE 2

|  | Comparative heat exchanger | Inventive heat exchanger |
| --- | --- | --- |
| Total rate of flow (l/min) | 17 | 18.9 |
| Pressure loss (mmHg) | 0.64 $Q^2$ | 0.5 $Q^2$ |

In Table 2, Q represents the rate of flow of the medium (l/mm).

Using the same heat exchanger as that of the second embodiment and the comparative heat exchanger, the heat-exchange efficiencies of the heat exchangers were measured when cow blood having a hemoglobin concentration of 12 g/dl was employed and water flowed at a rate of 15 l/min. The results are shown in FIG. 6, which indicates that the heat-exchanging efficiency of the heat exchanger of the present invention is better than that of the comparative heat exchanger.

The baffle plates 7, 7a are normally made of the same material as, or a material similar to, the housing 1. However, the material of the baffle plates 7, 7a is not limited to those materials. The configuration and number of the baffle plates 7, 7a may be varied insofar as the introduced fluid flows into the pipes 9 uniformly at a constant rate. The direction in which the baffle plates 7, 7a installed is not limited; they may be attached at any angle insofar as they can generate a turbulent fluid flow.

When the heat exchanger of the invention is in use, a heat medium flows through or around the pipes 9. However, if the heat exchanger is used as a heat exchanger associated with an artificial lung, it is preferable that blood flow around the pipes 9 and heat medium (cold water) flow through the pipes 9.

INDUSTRIAL APPLICABILITY

With the present invention, as described above, the baffle plates for producing a turbulent fluid flow are disposed in the head with the inlet port. No air bubbles remain trapped in the head, and the discharge pressures under which the fluid is discharged from the pipes are prevented from being fluctuated. The heat exchanger of the invention has a high heat-exchanging efficiency.

Although certain preferred embodiments have been shown and described, it should be understood that many changes and modifications may be made therein without departing from the scope of the appended claims.

We claim:

1. A multitube heat exchanger comprising:

a tubular body;

first and second partitions disposed on opposite ends of said tubular body;

a plurality of juxtaposed pipes extending between said partitions for passing one fluid through said pipes and between said partitions;

fluid inlet and outlet holes opening into said tubular body for passing another fluid around said pipes for effecting a heat exchange between the fluids through walls of said pipes;

first and second heads disposed respectively over said first and second partitions, and forming respective first and second cavities between said heads and their associated said partitions, at least said first head having a substantially circular cross-section, said pipes opening into said first and second cavities at opposite ends of said pipes;

a fluid inlet port opening into said first head and supplying said first fluid into said first cavity formed between said first head and its associated partition, said fluid inlet port being disposed substantially tangentially with respect to said circular cross-section of said first head so that a swirling motion is imparted to said one fluid entering into said first cavity through said fluid inlet port;

at least one baffle plate disposed in said first cavity of said first head and arranged spaced from said first partition for reducing the directivity of said one fluid introduced from said fluid inlet port and to substantially render uniform the rate of flow of said one fluid introduced into said pipes; and said fluid inlet port having a central axis, said fluid inlet port being disposed with respect to said at least one baffle plate such that a plane parallel to said first partition and containing said central axis does not intersect any part of said at least one baffle plate.

2. A multitube heat exchanger according to claim 1, wherein said at lest one baffle plate comprises a plurality of baffle plates for generating a turbulent flow in said one fluid introduced from said fluid inlet port, said baffle plates being disposed in said first cavity of said first head and being angularly spaced from each other.

3. A multitube heat exchanger according to claim 2, wherein each of said baffle plates projects radially outwardly from a center of said first head.

* * * * *

UNITED STATES PATENT AND TRADEMARK OFFICE
CERTIFICATE OF CORRECTION

PATENT NO. : 5,117,903
DATED : June 2, 1992
INVENTOR(S) : OSHIYAMA et al

It is certified that error appears in the above-identified patent and that said Letters Patent is hereby corrected as shown below:

Column 1, line 66, replace "there s" with --there is--.

Column 6, line 25 (claim 2), replace "at lest" with

--at least--.

Signed and Sealed this

Fifth Day of October, 1993

Attest:

BRUCE LEHMAN

*Attesting Officer*  *Commissioner of Patents and Trademarks*